US008470588B2

(12) United States Patent
Boehm et al.

(10) Patent No.: US 8,470,588 B2
(45) Date of Patent: Jun. 25, 2013

(54) ROTATABLE TEST ELEMENT

(75) Inventors: Christoph Boehm, Viernheim (DE); Norbert Oranth, Hirschberg (DE); Juergen Spinke, Lorsch (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 300 days.

(21) Appl. No.: 12/407,419

(22) Filed: Mar. 19, 2009

(65) Prior Publication Data

US 2009/0191643 A1 Jul. 30, 2009

Related U.S. Application Data

(63) Continuation of application No. PCT/EP2007/008419, filed on Sep. 27, 2007.

(30) Foreign Application Priority Data

Sep. 27, 2006 (EP) .................................... 06020219

(51) Int. Cl.

*G01N 33/53* (2006.01)
*G01N 31/22* (2006.01)
*G01N 21/00* (2006.01)
*G01N 9/30* (2006.01)
*G01N 21/75* (2006.01)

(52) U.S. Cl.

USPC .......... 435/287.2; 422/72; 422/414; 422/420; 422/82.05; 435/287.3; 435/287.7; 435/288.7; 436/44; 436/45

(58) Field of Classification Search

None

See application file for complete search history.

(56) References Cited

U.S. PATENT DOCUMENTS

| | | | |
|---|---|---|---|
| 4,861,711 A | 8/1989 | Friesen et al. | |
| 5,061,381 A | 10/1991 | Burd | |
| 5,242,606 A | 9/1993 | Braynin et al. | |
| 5,698,395 A * | 12/1997 | Ritterband et al. | 435/6.19 |
| 2002/0076354 A1 | 6/2002 | Cohen | |
| 2003/0207457 A1 | 11/2003 | Kopf-Sill et al. | |
| 2004/0265171 A1 | 12/2004 | Pugia et al. | |
| 2005/0014249 A1 | 1/2005 | Staimer et al. | |
| 2005/0037484 A1 | 2/2005 | Staimer et al. | |
| 2005/0109396 A1 | 5/2005 | Zucchelli et al. | |

FOREIGN PATENT DOCUMENTS

| | | |
|---|---|---|
| JP | 2006208183 A | 8/2006 |
| WO | 9958245 A1 | 11/1999 |
| WO | 02/074438 A2 | 9/2002 |
| WO | 2005001429 A2 | 1/2005 |
| WO | 2005009581 A1 | 2/2005 |
| WO | 2005009581 A2 | 2/2005 |

* cited by examiner

*Primary Examiner* — Neil N Turk

(74) *Attorney, Agent, or Firm* — Dinsmore & Shohl LLP

(57) ABSTRACT

A test element and method for detecting an analyte with the aid thereof is provided. The test element is essentially disk-shaped and flat, and can be rotated about a preferably central axis which is perpendicular to the plane of the disk-shaped test element. The test element has a sample application opening for applying a liquid sample, a capillary-active zone, in particular a porous, absorbent matrix, having a first end that is remote from the axis and a second end that is near to the axis, and a sample channel which extends from an area near to the axis to the first end of the capillary-active zone that is remote from the axis.

18 Claims, 6 Drawing Sheets

ROTATABLE TEST ELEMENT

BACKGROUND OF THE INVENTION

The present invention relates generally to analytical test devices and, more particularly, to a rotatable test element and method for detecting an analyte with the aid of the test element.

In principle the systems for analysing liquid sample materials or sample materials which can be converted into a liquid form can be divided into two classes. On the one hand, there are analytical systems which operate exclusively with so-called wet reagents and, on the other hand, there are systems which use so-called dry reagents. In particular in medical diagnostics and also in environmental and process analytics the former systems are primarily used in permanently equipped laboratories whereas the latter systems are used mainly for "on-site" analyses.

Analytical systems using dry reagents are offered in the field of medical diagnostics especially in the form of so-called test carriers, e.g., test strips. Prominent examples of this are test strips for determining the blood sugar value or test strips for urine analyses. Such test carriers usually integrate several functions (e.g., the storage of reagents in a dried form or, although more rare, in solution; the separation of undesired sample components in particular red blood corpuscles from whole blood; in the case of immunoassays the so-called bound free separation; the metering of sample volumes; the transport of sample liquid from outside a device into the interior of a device; the control of the chronological sequence of individual reaction steps, etc.). In this connection the function of sample transport is often effected by means of absorbent materials (e.g., papers or fleeces), by means of capillary channels or by using external driving forces (such as, e.g., pressure, suction) or by means of centrifugal force. Disk-shaped test carriers, so-called lab-disks or optical bio-disks pursue the idea of controlled sample transport by means of centrifugal force. Such disk-shaped, compact disk-like test carriers allow a miniaturization by utilizing microfluidic structures and at the same time enable processes to be carried out in parallel by the repeated application of identical structures for the parallel processing of similar analyses from one sample or of identical analyses from different samples. Especially in the field of optical bio-disks it is possible to integrate optically stored digital data for identifying the test carrier or for the control of analytical systems on the optical bio-disks.

In addition to miniaturization and parallelization of analyses and integration of digital data on optical disks, bio-disks generally have the advantage that they can be manufactured by established manufacturing processes and can be measured by means of an established evaluation technology. In the case of the chemical and biochemical components of such optical bio-disks it is usually possible to make use of known chemical and biochemical components. A disadvantage of the optical lab-disks or bio-disks that are based purely on centrifugal and capillary forces is that it is difficult to immobilize reagents and the accuracy of the detection suffers. Especially in the case of detection systems which are based on specific binding reactions, such as e.g., immunoassays, there is an absence of the volume component compared to conventional test strip systems especially in the so-called bound-free separation.

For this reason attempts have recently been made especially in the field of immunoassays to establish hybrids of conventional test strips and bio-disks. This results in bio-disks with channels and channel-like structures for liquid transport, on the one hand, and voluminous absorbent materials in these structures (at least partially), on the other hand.

A disadvantage of the concepts of the prior art is that a specific control of the reaction and dwelling times of the sample liquid after uptake of the reagents and after they have flowed into the porous, absorbent matrix is not possible especially for specific binding assays such as, e.g., immunoassays.

SUMMARY OF THE INVENTION

It is against the above background that the present invention provides certain unobvious advantages and advancements over the prior art. In particular, the inventors have recognized a need for improvements in rotatable test element design.

In accordance with one embodiment of the present invention, a test element which is essentially disk-shaped is provided comprising an axis within the test element which is perpendicular to the plane of the test element and about which the test element can be rotated, a sample application opening for applying a liquid sample, a capillary-active zone having a first end that is remote from the axis and a second end that is near to the axis, and a sample channel which extends from the sample application opening over an area near to the axis to the first end of the capillary-active zone that is remote from the axis.

In accordance with another embodiment of the present invention, a test element is provided comprising a sample application opening, a sample metering zone and a zone for sample excess, the sample application opening being in contact with the sample metering zone and the zone for sample excess, wherein a capillary stop is present between the sample metering zone and the zone for sample excess.

In accordance with yet another embodiment of the present invention, a method for detecting an analyte in a liquid sample is provided comprising applying the sample to the sample application opening of the test element according to an embodiment of the present invention, rotating the test element such that the sample is transported to the end of the capillary-active zone that is remote from the axis, stopping or slowing the rotation of the test element to such an extent that the sample or a material obtained from the sample when it flows through the test element is sucked from the end remote from the axis to the end near to the axis of the capillary-active zone, and detecting the analyte visually or optically in the capillary-active zone or in a zone downstream thereof.

In accordance with still another embodiment of the present invention, system for determining an analyte in a liquid sample is provided comprising a test element according to an embodiment of the present invention and a measuring device, wherein the measuring device has at least one drive for rotating the test element and an evaluation optics for evaluating the visual or optical signal of the test element.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, wherein like structure is indicated with like reference numerals and in which.

Figure 1:
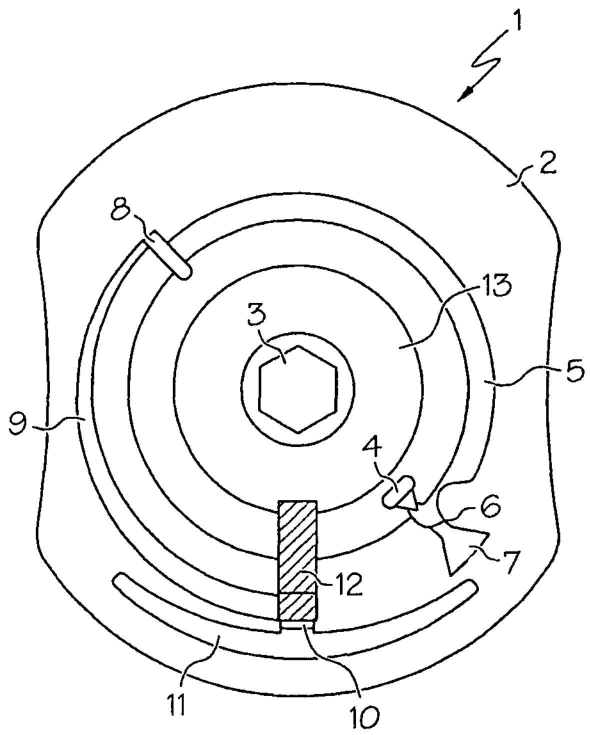
FIG. 1 shows a schematic top-view of a test element in accordance with an embodiment of the present invention.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

The test element according to the invention is essentially disk-shaped and flat. It can be rotated about a preferably central axis which is perpendicular to the plane of the disk-shaped test element within the test element. The test element is typically a circular disk comparable to a compact disk. However, the invention is not limited to this form of disk but rather can also readily be used for non-symmetrical or non-circular disks.

With regard to components the test element firstly contains a sample application opening into which a liquid sample can be pipetted or introduced in another manner. The sample application opening can either be near to the axis (i.e., near to the center of the disk) or remote from the axis (i.e., near to the edge of the disk). In the case that the sample application opening is remote from the axis, the test element contains at least one channel which can transfer the liquid sample from the position remote from the axis into a position near to the axis by means of capillary forces.

In this connection the sample application opening can directly discharge into a sample channel. However, it is also possible that the sample application opening firstly leads into a reservoir that is located behind it into which the sample flows before it flows further into the sample channel. It can be ensured by suitable dimensions that the sample flows from the sample application opening into the subsequent fluidic structures without further assistance. This may require a hydrophilization of the surfaces of the fluidic structures and/or the use of structures which enhance the formation of capillary forces. It is, however, also possible to only allow the fluidic structures of the test element according to the invention to be filled from the sample application opening after an external force, typically a centrifugal force acts on it.

The test element additionally contains a capillary-active zone typically in the form of a porous, absorbent matrix or capillary channel which holds at least a portion of the liquid sample. The capillary-active zone has a first end remote from the axis and a second end near to the axis.

In addition the test element has a sample channel which extends from the sample application opening to the first end of the capillary-active zone remote from the axis and in particular to the porous, absorbent matrix. In this case the sample channel passes at least once through a region near to the axis which is nearer to the preferably central axis than the first end of the capillary-active zone that is remote from the axis.

One feature of the test element of the present invention is that the capillary-active zone, and in particular the porous, absorbent matrix, has a second end that is near to the axis. The first end of the capillary-active zone that is remote from the axis is in contact with the sample channel in which the sample can be moved by means of capillary forces and/or centrifugal forces and/or other external forces such as overpressure or negative pressure. As soon as the liquid sample reaches the first end of the capillary-active zone remote from the axis, optionally after uptake of reagents and/or dilution media and/or pre-reactions have occurred, it is taken up into the said zone and transported through the said zone by capillary forces (which in the case of a porous, absorbent matrix can also be referred to as suction forces).

The capillary-active zone is typically a porous, absorbent matrix and in particular can be a paper, a membrane or a fleece.

The capillary-active zone and in particular the porous, absorbent matrix can contain one or more zones containing immobilized reagents.

Specific binding reagents for example specific binding partners such as antigens, antibodies, (poly) haptens, streptavidin, polystreptavidin, ligands, receptors, nucleic acid strands (capture probes) and such like are typically immobilized in the capillary-active zone and in particular in the porous, absorbent matrix. They are used to specifically capture the analyte or species derived from the analyte or related to the analyte from the sample flowing through the capillary-active zone. These binding partners can be present immobilized in or on the material of the capillary-active zone in the form of lines, points, patterns or they can be indirectly bound to the capillary-active zone e.g., by means of so-called beads. Thus, for example, in the case of immunoassays one antibody against the analyte can be present immobilized on the surface of the capillary-active zone or in the porous, absorbent matrix which then captures the analyte (in this case an antigen or hapten) from the sample and also immobilizes it in the capillary-active zone such as, e.g., the absorbent matrix. In this case the analyte can be made detectable for example by means of a label that can be detected visually, optically or fluorescence-optically by further reactions, for example by additionally contacting it with a labelled bindable partner.

In one embodiment of the test element according to the invention, the second end near to the axis of the capillary-active zone and in particular of the porous, absorbent matrix adjoins a further absorbent material or an absorbent structure such that it can take up liquid from the zone. The porous, absorbent matrix and the further material typically slightly overlap for this purpose. The further material or the further absorbent structure serve on the one hand, to assist the suction action of the capillary-active zone and in particular of the porous, absorbent matrix and, on the other hand, serve as a holding zone for liquid which has already passed through the capillary-active zone. In this connection the further material can consist of the same materials or different materials than the matrix. For example, the matrix can be a membrane and the further absorbent material can be a fleece or a paper. Other combinations are of course equally possible.

The test element according to the invention is characterized in one embodiment by the fact that the sample channel contains zones of different dimensions and/or for different functions. For example, the sample channel can contain a zone which contains reagents that are soluble in the sample or can be suspended in the sample. These reagents can be dissolved or suspended in the liquid sample when it flows into or through the channel and can react with the analyte in the sample or with other sample components.

The different zones in the sample channel can also differ in that there are zones with capillary activity and those without capillary activity. Moreover, there may be zones having a high hydrophilicity and those with a low hydrophilicity. The individual zones can quasi seamlessly merge into one another or be separated from one another by certain barriers such as valves and in particular non-closing valves such as geometric valves or hydrophobic barriers.

The reagents in the sample channel are typically present in a dried or lyophilized form. It is, however, also possible that the reagents are present in the test element according to the invention in a liquid form.

The reagents can be introduced into the test element in a known manner. The test element typically contains at least two layers, a bottom layer into which the fluidic structures are introduced and a cover layer which apart from inlet openings for liquids and vent openings, contains no further structures. The introduction of reagents during the manufacture of the test device is usually carried out before the upper part of the test element (cover layer) is mounted on the lower part (bottom layer). At this point in time the fluidic structures are open in the lower part so that the reagents can be easily metered in a liquid or dried form. In this connection the reagents can for example be introduced by pressing or dispensing. However, it is also possible to introduce the reagents into the test element by impregnating them in absorbent materials such as papers, fleeces or membranes which are inserted into the test element. After placing the reagents and inserting the absorbent materials, for example the porous, absorbent matrix (membrane) and optionally further absorbent materials (waste fleece, etc.), the upper and lower part of the test element are joined together, for example, clipped, welded, glued and such like.

Alternatively the bottom layer may also have the inlet openings for liquids and the vent openings in addition to the fluidic structures. In this case the cover layer can be formed completely without openings optionally with exception of a central opening to receive a drive unit. In this case in particular the cover part can simply consist of a plastic foil which is glued onto the lower part or welded to it.

The sample channel usually contains a zone for separating particulate components from the liquid sample. Especially if blood or other body fluids containing cellular components are used as a sample material, this zone serves to separate the cellular sample components. Thus, almost colorless plasma or serum which is usually more suitable than strongly colored blood for subsequent visual or optical detection methods can be obtained by separating especially the red corpuscles (erythrocytes) from the blood.

Cellular sample components are typically separated by centrifugation, i.e., by rapidly rotating the test element after filling it with liquid sample. For this purpose the test element according to the invention contains channels and/or chambers of suitable dimensions and geometric designs. In particular, the test element can contain an erythrocyte collecting zone (erythrocyte chamber or erythrocyte trap) for the separation of cellular blood components and a serum or plasma collection zone (serum or plasma chamber).

In order to control the flow of sample liquid in the test element, it can contain valves especially in the sample channel and in particular so-called non-closing or geometric valves or hydrophobic barriers. These valves serve as capillary stops. They can ensure a specific chronological and spatial control of the sample flow through the sample channel and individual zones of the test element.

In particular, the sample channel can have a sample metering zone which allows an accurate measurement of the sample which is firstly applied in excess. In a typical embodiment, the sample metering zone extends from the sample application opening over an appropriate piece of sample channel up to a valve in the fluidic structure, in particular a geometric valve or a hydrophobic barrier. In this connection the sample application opening can firstly receive an excess of sample material. The sample flows from the sample application zone into the channel structure driven either by capillary forces or by centrifugation and fills it up to the valve. Excess sample initially remains in the sample application zone. Only when the channel structure is filled up to the valve, will a sample excess chamber adjoining the sample application zone and branching from the sample channel be filled for example by capillary forces or by centrifuging the test element. In this case it must be ensured that the sample volume to be measured is initially not transported beyond the valve by means of a suitable choice of valve. Once excess sample has been collected in the corresponding overflow chamber, there is an exactly defined sample volume between the valve of the sample channel on one side and the inlet to the sample overflow chamber on the other side. This defined sample volume is then moved beyond the valve by applying external forces and in particular by starting a further centrifugation. All fluidic areas which are located after the valve and which come into contact with sample are then firstly filled with an exactly defined sample volume.

The sample channel can additionally have an inlet for further liquids apart from the sample liquid. For example a second channel which for example can be filled with a washing liquid or reagent liquid, can discharge into the sample channel.

The system according to the invention consisting of measuring device and test element is used to determine an analyte in a liquid sample. In this case the measuring device comprises among others at least one drive for rotating the test element and evaluation optics for evaluating the visual or optical signal of the test element.

The optical system of the measuring device can typically be used to measure fluorescence with spatially resolved detection. In the case of two-dimensional, i.e., planar evaluation optics, an LED or a laser is typically used to illuminate the detection area of the test element and optionally to excite optically detectable labels. The optical signal is detected by means of a CMOS or CCD (typically with 640×480 pixels). The light path is direct or folded (e.g., via mirrors or prisms).

In the case of anamorphotic optics the illumination or excitation is typically by means of an illumination line which illuminates the detection area of the test element typically perpendicular to the detection and control lines. In this case the detection can be by means of a diode line. A rotary movement of the test element can in this case be utilized to illuminate and evaluate the second dimension in order to thus scan the planar area to be evaluated with the diode line.

A DC motor with an encoder or a step motor can be used as the drive to rotate and position the test element.

The temperature of the test element is typically maintained indirectly in the device for example by heating or cooling the plate on which the disk-shaped test element rests in the device. The temperature is typically measured in a contactless manner.

The method according to the invention serves to detect an analyte in a liquid sample. The sample is firstly applied to the sample application opening of the test element. Subsequently the test element is rotated typically about its preferably central axis; it is, however, also possible to carry out the method according to the invention such that the rotation is about another axis which may also be outside the test element. In this process the sample is transported from the sample application opening to the end of the capillary-active zone and in particular of the porous, absorbent matrix that is remote from the axis. The rotation of the test element is then slowed down or stopped to such an extent that the sample or a material obtained from the sample as it flows through the test element (for example a mixture of sample and reagents, a sample changed by pre-reactions with reagents from the test element, a sample freed of certain components such as serum or plasma from whole blood after separation of erythrocytes, etc.) is transported from the end of the capillary-active zone and in particular of the porous, absorbent matrix that is remote from the axis to the end that is near to the axis. The analyte is finally visually or optically detected in the capillary-active zone, in particular in the porous, absorbent matrix or in a zone downstream thereof.

It is possible to exactly determine and control the time at which the sample (or a material obtained from the sample) starts to migrate through the capillary-active zone by specifically slowing down or stopping the rotation of the test element. A movement of the sample into and through the capillary-active zone is only possible when the magnitude of the capillary force (suction force) in the capillary-active zone exceeds the magnitude of the opposing centrifugal force. Liquid transport in the capillary-active zone can be specifically started in this manner. For example, it is thus possible to await a possible pre-reaction or pre-incubation of the sample or an incubation of the sample before the rotation of the test element is slowed down or stopped to such an extent that the sample is able to flow into the capillary-active zone.

The transport of the sample (or of a material obtained from the sample) through the capillary-active zone can be specifically slowed down or stopped by a new rotation of the test element about its preferably central axis. The centrifugal forces occurring during the rotation counteract the capillary force which moves the sample liquid from the end remote from the axis of the capillary-active zone to the end near to the axis. Thus, a specific control and in particular slowing down of the flow rate of the sample in the capillary-active zone is possible even to the extent of a reversal of the flow direction. In this manner it is possible to for example control the residence time of the sample in the capillary-active zone.

In particular it is also possible with the test element and the method according to the invention to reverse the direction of migration of the liquid sample and/or of another liquid through the capillary-active zone by the rotation of the test element wherein this can be carried out several times to achieve a reciprocating movement of the liquid. By means of a concerted interplay of capillary forces which transport the liquid in the capillary-active zone from the outside (i.e., from the end remote from the axis) towards the inside (i.e., towards the end near to the axis) and opposing centrifugal forces, it is possible among others to increase the binding efficiency of the binding reactions in the capillary-active zone, to improve the dissolution of soluble reagents and mix them with the sample or other liquids, or to increase the washing efficiency (bound-free separation) in the case of affinity assays.

In particular, in connection with immunoassays the detection can be carried out according to the principle of a sandwich assay or in the form of a competitive test.

It is also possible that a further liquid is applied to the test element after the rotation of the test element, said liquid being transported after the sample from the end of the capillary-active zone and in particular of the porous, absorbent matrix that is remote from the axis to the end that is near to the axis.

The further liquid can be in particular a buffer, typically a washing buffer or a reagent liquid. The addition of the further liquid can result in an improved signal to background ratio compared to conventional test strips especially in relation to immunoassays because the addition of liquid can be used as a washing step after the bound-free separation.

Although the present invention is not limited to specific advantages or functionality, it is noted that the combination of liquid transport by means of centrifugal forces and by means of suction forces in capillary-active zones and in particular in porous, absorbent matrix materials allows a precise control of liquid flows. According to the invention the capillary-active zone and in particular the porous, absorbent matrix transports the liquid from an end remote from the axis to an end near to the axis, i.e., from the periphery of the disk-shaped test element towards the axis of rotation. The centrifugal force which can also be used to move the liquids, exactly counteracts this transport direction. Systematic control of the rotation of the test element (such as, e.g., more rapid/slower rotation, switching the rotary movement on and off) therefore enables the flow of sample liquid in the capillary-active zone and in particular in the porous, absorbent matrix to be slowed down or stopped thus allowing selective and defined reaction conditions to be maintained. At the same time the use of the porous, absorbent matrix which essentially serves as a capture matrix for the bound-free separation in immunoassays, allows an efficient capture of sample components during the course of the immunoassay. In particular the interplay of centrifugal and capillary forces (suction forces) enables the sample to be moved backwards and forwards over a reagent zone, in particular a zone containing immobilized reagents (especially a capture zone for heterogeneous immunoassays) without an increased amount of technical complexity and thus ensures a more effective dissolution of the reagents, mixing of the sample with reagents or a capture of sample components on immobilized binding partners. At the same time it is possible to eliminate depletion effects when sample components (above all the analyte) bind to immobilized binding partners and thus increase the binding efficiency (i.e., sample components depleted in analyte can be replaced by analyte-rich sample components by a reciprocating movement of sample over the capture zone and/or by efficient mixing). Moreover, the reciprocating movement of liquids in the capillary-active zone can result in the most efficient utilization of the small liquid volumes not only for reaction purposes (in this case the sample volume in particular is utilized) but also for washing purposes, for example in order to improve the discrimination between bound and free label in the capture zone. This allows an effective reduction of the amounts of sample and liquid reagents as well as of washing buffer.

The preferably central position of the axis of rotation within the test element enables the test element itself as well as the associated measuring device to be designed as compactly as possible. In the case of chip-shaped test elements such as those shown for example in FIGS. 1 and 2 of US 2004/0265171 the axis of rotation is outside the test element. An associated turntable or rotor is thus inevitably larger than in the case of a test element with identical dimensions but where the axis of rotation is within the test element and is preferably arranged centrally as is the case with the test elements according to the invention.

The invention is further elucidated by the following examples and figures. In this case reference is made to immunological sandwich assays. However, the invention is not limited thereto. It can also be applied to other types of immunoassays and in particular also to competitive immunoassays or other types of specific binding assays (for example those which use sugars and lectins, hormones and their receptors or also complementary nucleic acid pairs as binding partners). Typical representatives of these specific binding assays are known to a person skilled in the art (with regard to immunoassays reference is explicitly made to FIGS. 1 and 2 and the accompanying passages in the description of the document U.S. Pat. No. 4,861,711) and can be readily applied to the present invention. In the following examples and figures a porous, absorbent matrix (membrane) is described as a typical representative of the capillary-active zone. However, the invention is not limited to such a matrix. It is for example possible to use a capillary-active channel which can also have microstructures for controlling the liquid flows or for providing or immobilizing reagents or for mixing liquids and/or reagents instead of the matrix.

FIG. 1 shows a top-view of a typical embodiment of the test element according to the invention in a schematic diagram. For the sake of clarity only the layer of the test element is shown which contains the fluidic structures. The embodiment shown contains only one opening for introducing sample and/or washing liquid. In this embodiment interfering sample components are separated after the sample has been contacted with reagents.

Figure 2:
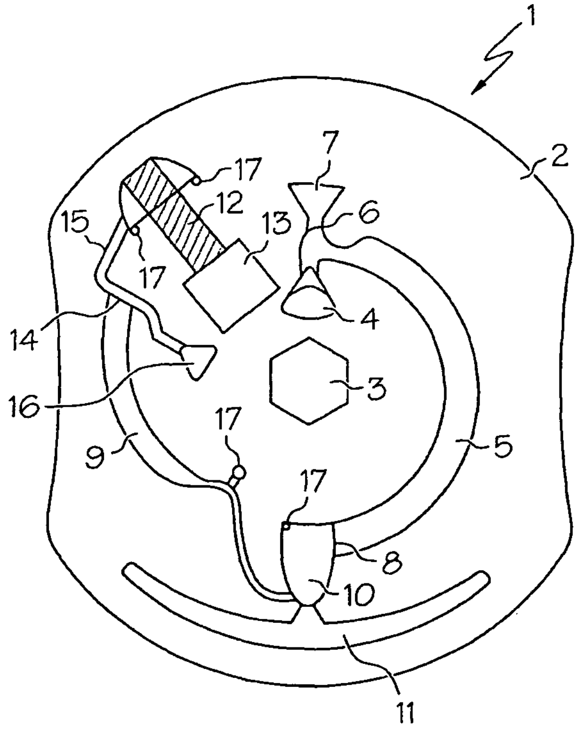
FIG. 2 shows schematically a test element in accordance with another embodiment of the present invention.

FIG. 2 shows schematically a further typical embodiment of the test element according to the invention. Also in this case only the structure is shown which has the fluidic elements of the test element. In this embodiment of the test element there are two separate sample and washing buffer application openings. In this case the cellular sample components are separated before the sample is brought into contact with reagents.

Figure 3:
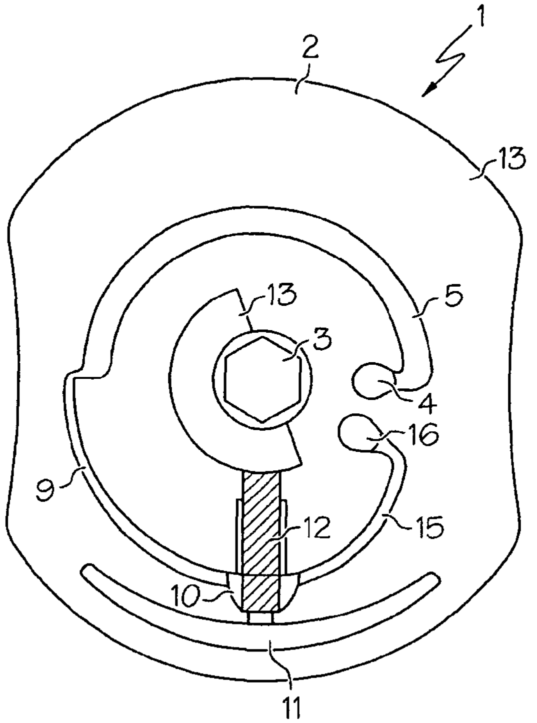
FIG. 3 shows schematically a variant of the test element shown in FIG. 1.

FIG. 3 shows a variant of the embodiment according to FIG. 1 in a schematic diagram. Also in this case the cellular sample components are separated after the sample has been brought into contact with reagents. However, the structure according to FIG. 3 has a separate feed for washing liquid.

Figure 4:
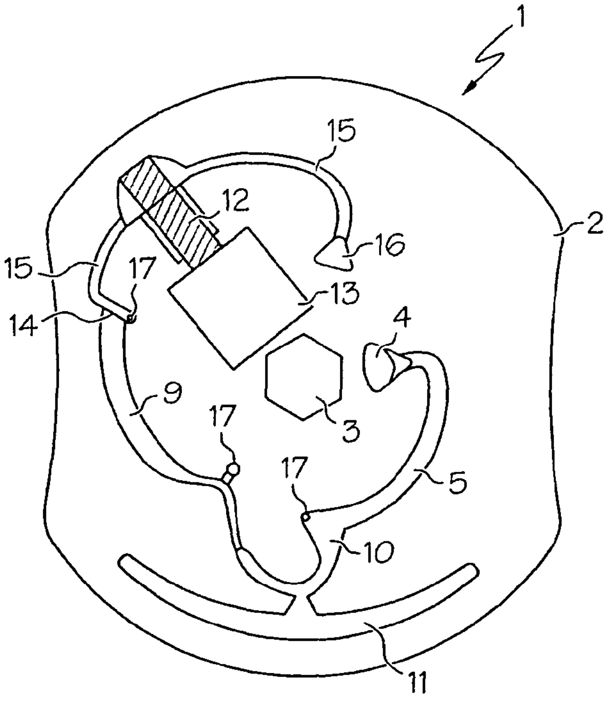
FIG. 4 shows schematically a test element in accordance with yet another embodiment of the present invention.

FIG. 4 shows a further typical embodiment of the test element according to the invention in a schematic view similar to FIG. 2.

Figure 5:
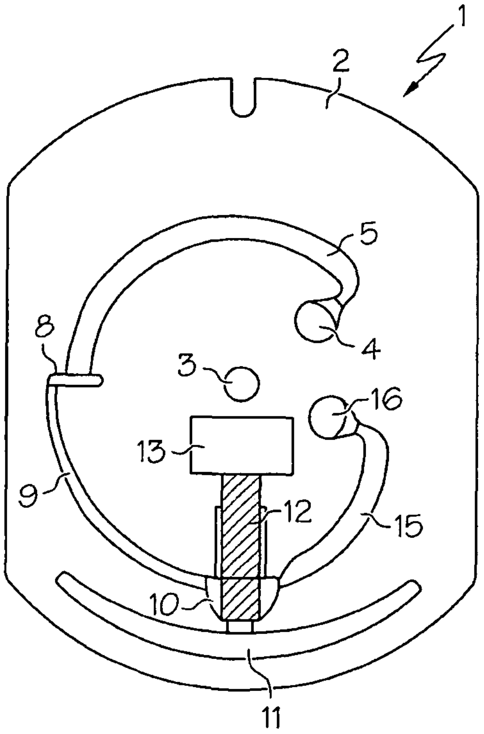
FIG. 5 shows a variant of the test element shown in FIG. 3.

FIG. 5 shows a slight further development of the test element according to FIG. 3. In contrast to the embodiment according to FIG. 3, FIG. 5 has a different geometric arrangement of the waste fleece and a different type of valve at the end of the sample metering section.

Figure 6:
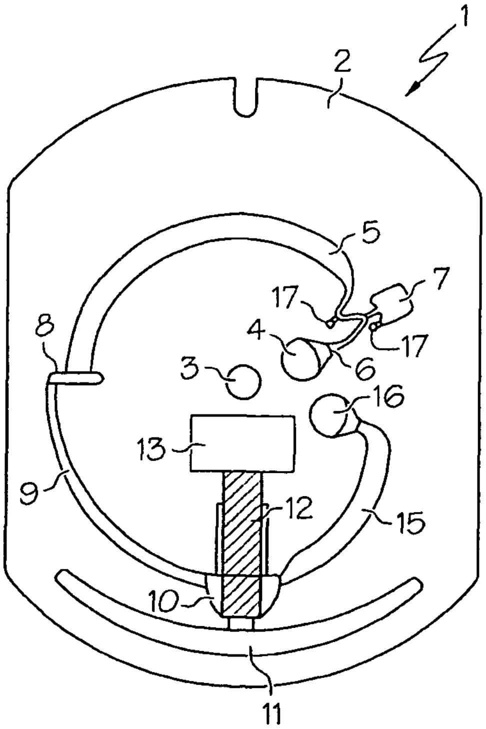
FIG. 6 shows schematically a top-view of a variant of the test element shown in FIG. 5.

FIG. 6 shows schematically a top-view of a further development of the test element according to FIG. 5. In contrast to the embodiment according to FIG. 5, the embodiment according to FIG. 6 has a fluidic structure for receiving sample excess.

Figure 7:
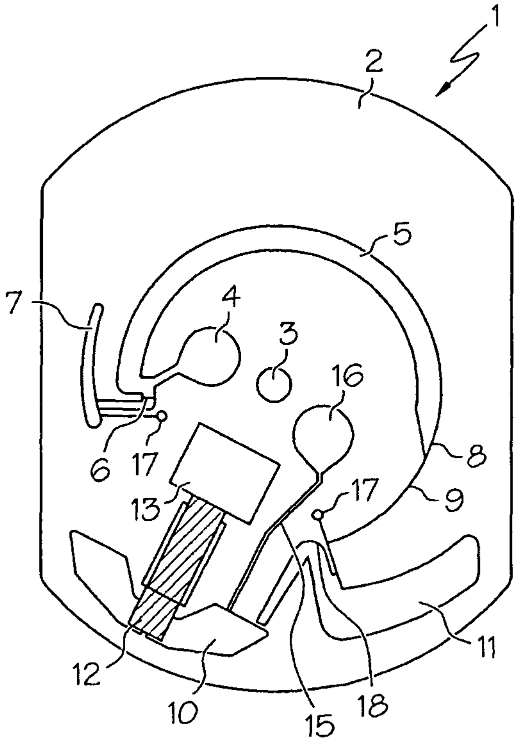
FIG. 7 shows another variant of the test element shown in FIG. 3.

FIG. 7 is a schematic representation of a further variant of the test element according to FIG. 3. The fluidic structures are functionally essentially similar to those of FIG. 3. However, their geometric alignment and design are different.

Figure 8:
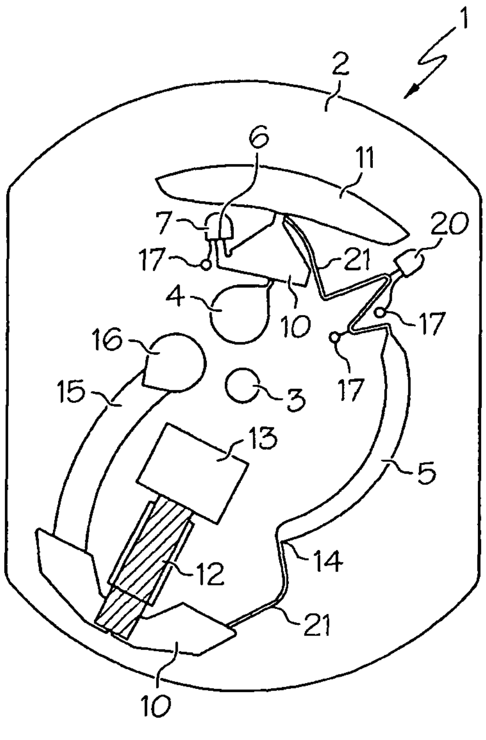
FIG. 8 shows a schematic top-view of a test element in accordance with yet still another embodiment of the present invention.

FIG. 8 shows schematically a further typical embodiment of the test element according to the invention. The structures in FIG. 8 correspond essentially to the functions that are already known from the test element according to FIG. 4.

Figure 9:
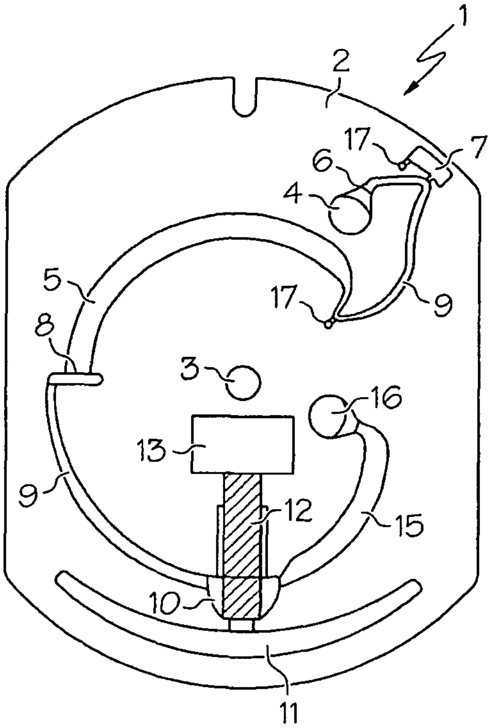
FIG. 9 shows a schematic top-view of a variant of the test element shown in FIG. 6.

FIG. 9 shows schematically a top-view of an alternative to the test element according to FIG. 6. In contrast to the embodiment according to FIG. 6, the embodiment according to FIG. 9 has a sample application opening which is remote from the axis which firstly moves the sample via a capillary nearer to the center of the test element i.e., into an area near to the axis.

Figure 10:
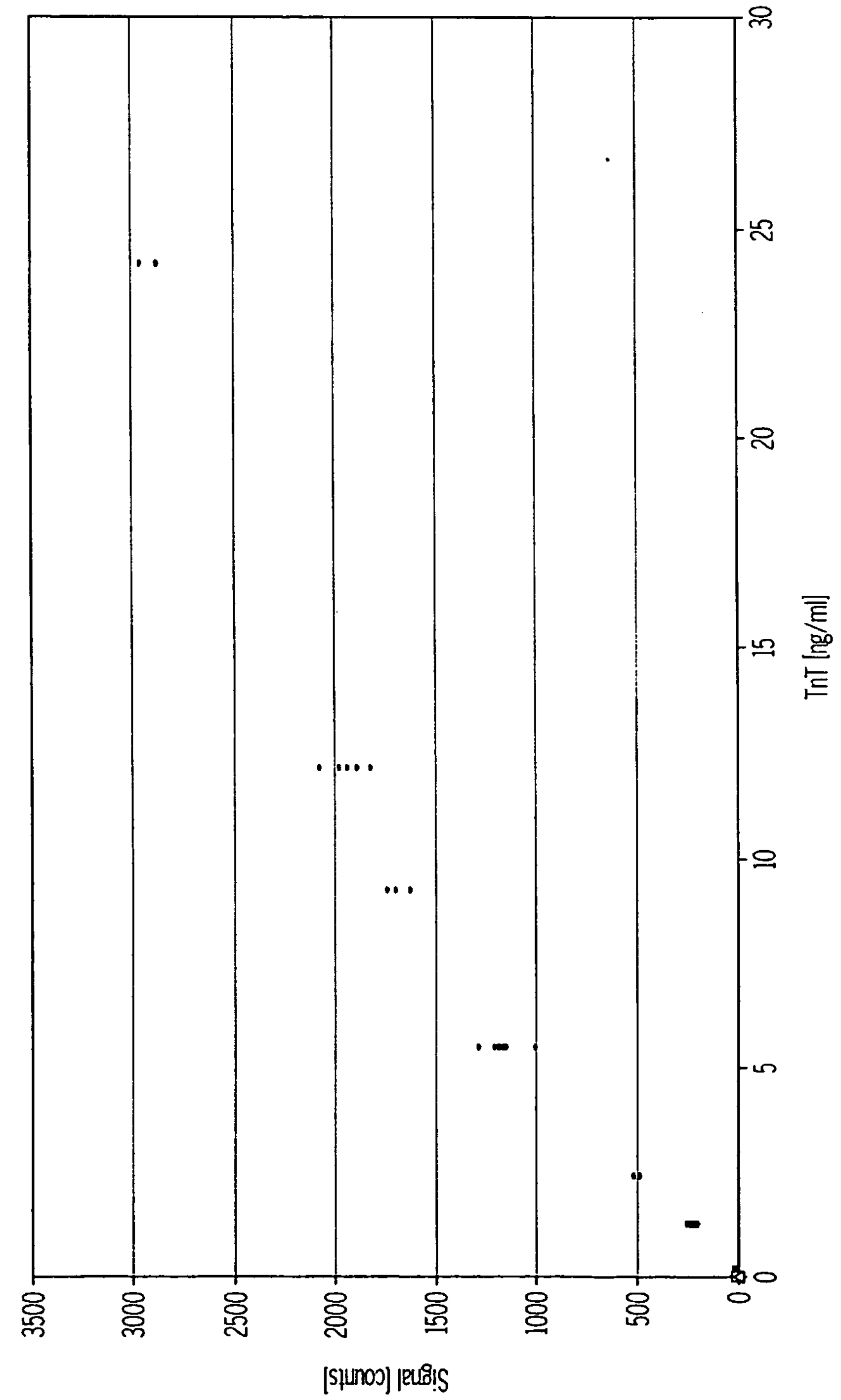
FIG. 10 shows the concentration of troponin T in ng/ml plotted against the signal strength (counts).

FIG. 10 shows a typical curve shape for troponin T measurements in whole blood samples (concentration of troponin T in ng/ml plotted against the signal strength (counts)). Recombinant troponin T was added to the samples to yield the respective concentrations. The data are from example 2 and were obtained with the aid of test elements according to FIG. 6/example 1.

The numerals and abbreviations in the figures have the following meaning:

| | |
|---|---|
| 1 | disk-shaped test element (disk) |
| 2 | substrate (e.g., one-piece or multipart, injection moulded, milled, composed of layers, etc.) |
| 3 | central opening (drive hole) |
| 4 | sample application opening |
| 5 | sample metering zone (metering section of the channel) |
| 6 | capillary stop (e.g., hydrophobic barrier, geometric/non-closing valve) |
| 7 | container for sample excess |
| 8 | capillary stop (e.g., hydrophobic barrier, geometric/non-closing valve) |
| 9 | channel |
| 10 | serum/plasma collecting zone (serum/plasma chamber) |
| 11 | erythrocyte collecting zone (erythrocyte chamber) |
| 12 | porous, absorbent matrix (membrane) |
| 13 | waste (fleece) |
| 14 | capillary stop (e.g., hydrophobic barrier, geometric/non-closing valve) |
| 15 | channel |
| 16 | opening for adding further liquids, e.g., washing buffer |
| 17 | vent hole |
| 18 | decanting channel |
| 19 | capillary stop (e.g., hydrophobic barrier, geometric/non-closing valve) |
| 20 | capture reservoir |
| 21 | capillary channel |

FIGS. 1 to 9 show different typical embodiments of the test element (1) according to the invention. Essentially the substrate (2) containing the fluidic structures and the central opening (drive hole 3) are shown in each case. In addition to the substrate that can for example be one piece or multipart and can be configured by means of injection molding, milling or by laminating appropriate layers, the disk-shaped test element (1) according to the invention also usually contains a cover layer which is not shown in the figures for the sake of clarity. The cover layer can in principle also carry structures but it usually has no structures at all apart from the openings for the samples and/or other liquids that have to be applied to the test element. The cover layer can also be designed completely without openings, for example in the form of a foil which is joined to the substrate and closes the structures located therein.

The embodiments which are shown in FIGS. 1 to 9 show fluidic structures which fulfil to a large extent the same functions even if they differ in detail from embodiment to embodiment. The basic configuration and the basic function is therefore elucidated in more detail on the basis of the embodiment according to FIG. 1. The embodiments according to FIGS. 2 to 9 are subsequently elucidated in more detail only on the basis of the specific differences between one another in order to avoid unnecessary repetition.

FIG. 1 shows a first typical embodiment of the disk-shaped test element (1) according to the invention. The test element (1) contains a substrate (2) which contains the fluidic and microfluidic as well as chromatographic structures. The substrate (2) is covered by a corresponding counterpiece (cover layer) (not shown) which contains sample application and vent openings which correspond with structures in the substrate (2). The cover layer as well as the substrate (2) have a central opening (3) which enables the disk-shaped test element (1) to be rotated by interaction with a corresponding drive unit in the measuring device. Alternatively the test element (according to one of the FIGS. 1 to 9) may have no such central opening (3) and the drive is rotated by a drive unit of the measuring device corresponding to the outer contours of the test element such as a rotating plate into which the test element is inserted into a depression corresponding to its shape.

The sample liquid, in particular whole blood, is applied to the test element (1) via the sample application opening (4). The sample liquid fills the sample metering zone (5) which is driven by capillary forces and/or centrifugal forces. The sample metering zone (5) can in this connection also contain dried reagents. It is delimited by the capillary stops (6 and 8) which can for example be in the form of a hydrophobic barrier or a geometric/non-closing valve. The delimitation of the sample metering zone (5) by the capillary stops (6, 8) ensures that a defined sample volume is taken up and passed into the fluidic zones that are located downstream of the sample metering zone (5). When the test element (1) is rotated, any sample excess is transferred from the sample application opening (4) and the sample metering zone (5) into the container for sample excess (7) whereas the measured amount of sample is transferred from the sample metering zone (5) into the channel (9).

The separation of red blood corpuscles and other cellular sample components is started in channel (9) at an appropriate speed of rotation. The reagents contained in the sample metering zone (5) are already present dissolved in the sample when the sample enters the channel (9). In this connection the entry of the sample into channel (9) via the capillary stop (8) results in a mixing of the reagents in the sample.

The time control of the rotation processes that is possible with the test element according to the invention allows a selective control of the residence times and thus of the incubation time of sample with reagents and of the reaction times.

During the rotation, the reagent-sample mixture is conducted into the fluidic structures (10) (serum/plasma collection zone) and (11) (erythrocyte collection zone). Due to the centrifugal forces which act on the reagent-sample mixture, plasma or serum is separated from the red blood corpuscles. In this process the red blood corpuscles collect in the erythrocyte collection zone (11) whereas the plasma remains essentially in the collection zone (10).

In contrast to test elements which use membranes or fleeces to separate particulate sample components (for example glass fiber fleeces or asymmetric porous plastic membranes to separate red blood corpuscles from whole blood, generally referred to as blood separating membranes or fleeces), the sample volume can be much more effectively utilized with the test elements according to the invention because virtually no dead volumes (e.g., volumes of the fiber interstices or pores) are present from which the sample can no longer be removed. Furthermore, some of these blood separating membranes and fleeces of the prior art have the undesired tendency to adsorb sample components (e.g., proteins) or to destroy (lyse) cells which is also not observed with the test elements according to the invention.

If the rotation of the test element (1) is stopped or slowed down, the reagent-plasma mixture (in which in the case of an immunoassay, sandwich complexes of analyte and antibody conjugates have for example formed in the presence of the analyte) is taken up into the porous, absorbent matrix (12) by its suction action and passed through this matrix. In the case of immunoassays the analyte-containing complexes are captured in the detection zone by the immobilized binding partners which are present in the membrane (12) and unbound, labelled conjugate is bound in the control zone. The fleece (13) adjoining the porous, absorbent matrix assists the movement of the sample through the membrane (12). The fleece (13) additionally serves to receive the sample after it has flowed through the membrane (12).

After the liquid sample has flowed through the fluidic structure of the test element (1) from the sample application opening (4) up to the fleece (13), washing buffer is pipetted into the sample application opening (4) in a subsequent step. As a result of the same combination of capillary, centrifugal and chromatographic forces the washing buffer flows through the corresponding fluidic structures of the test element (1) and washes in particular the membrane (12) where the bound analyte complexes are now located and thus removes excess reagent residues. The washing step can be repeated once or several times in order to thus improve the signal-to-background-ratio. This allows an optimization of the detection limit for the analyte and an increase of the dynamic measuring range.

The sample channel in which the liquid sample is transported in the test element (1) from the sample application opening (4) to the first end of the membrane (12) that is remote from the axis, comprises in the present case the sample metering zone (5), the capillary stop (8), the channel (9), the serum/plasma collection zone (10) and the erythrocyte chamber (11). In other embodiments the sample channel can consist of more or fewer single zones/areas/chambers.

FIGS. 3, 5, 6, 7 and 9 show essentially analogous embodiments to FIG. 1. FIG. 3 differs from FIG. 1 in that, on the one hand, no container for sample excess (7) is attached to the sample application opening (4) and no capillary stop is present at the end of the sample metering section (5) (i.e., a metered sample application is necessary in this case) and, on the other hand, in that a separate application opening (16) for further liquids such as, e.g., washing buffer and an associated channel (15) are present which can transport the buffer to the membrane (12). The transport of the buffer to the membrane (12) can in this case be based on capillary forces or centrifugal forces.

The embodiment according to FIG. 5 is substantially identical to the embodiment according to FIG. 3. The two embodiments differ only in the form of the waste fleece (13) and the fact that the test element according to FIG. 5 has a capillary stop (8) at the end of the sample metering section (5).

The embodiment according to FIG. 6 is again essentially identical to the embodiment according to FIG. 5 and differs from this by the additional presence of a container for sample excess (7) in the area between the sample metering opening (4) and the sample metering zone (5). In this case a metered application of the sample is not necessary (similar to FIG. 1).

The embodiment of the test element (1) according to the invention according to FIG. 7 essentially corresponds to the test element (1) of FIG. 6. Both embodiments have the same fluidic structures and functions. Only the arrangement and geometric design are different. The embodiment according to FIG. 7 has additional vent openings (17) which are necessary due to the different dimensions of the fluidic structures compared to FIG. 6 in order to enable the structures to be filled with samples or washing liquid. In this case channel (9) is designed as a thin capillary which is not filled until the test element rotates (i.e., the capillary stop (8) can only be overcome by means of centrifugal force). With the test element (1) according to FIG. 7 it is possible to already discharge collected plasma from the erythrocyte collection zone (11) during rotation; a decanting unit (18) is used for this purpose which finally ends in the serum/plasma collection zone (10).

The embodiment of the test element (1) according to the invention according to FIG. 9 essentially corresponds to the test element (1) of FIG. 6. Both embodiments have the same fluidic structures and functions. Only the arrangement and geometric design are different. The embodiment according to FIG. 9 basically has a sample application opening (4) that is located further to the outside, i.e., remote from the axis. This may be an advantage when the test element (1) is already placed in a measuring device in order to fill it with sample. In this case the sample application opening (4) can be made more easily accessible to the user than is possible with test elements according to FIGS. 1 to 8 where the sample application opening (4) is in each case arranged near to the axis (i.e., remote from the outer edge of the test element).

In contrast to the embodiment according to FIGS. 1, 3, 5, 6, 7 and 9, in the case of the embodiment according to FIGS. 2, 4 and 8 the cellular sample components are separated from the sample liquid before the sample comes into contact with reagents. This has the advantage that the use of whole blood or plasma or serum as the sample material does not lead to different measuring results because always plasma or serum firstly comes into contact with the reagents and the dissolution/incubation/reaction behavior should thus be virtually the same. Also in the embodiments according to FIGS. 2, 4 and 8, the liquid sample is firstly applied to the test element (1) via the sample application opening (4). The sample is subsequently transported further from the sample application opening (4) into the channel structures by capillary forces and/or centrifugal forces. In the embodiments according to FIGS. 2 and 4 the sample is transferred into a sample metering section (5) after application into the sample application opening (4) and subsequently serum or plasma is separated from whole blood by rotation. The undesired cellular sample components which are essentially erythrocytes, collect in the erythrocyte trap (11) whereas serum or plasma collects in the zone (10). The serum is removed from the zone (10) via a capillary and transported further into the channel structure (9) where dry reagents are accommodated and dissolved when the sample flows in. The sample-reagent mixture can overcome the capillary stop (14) from the channel structure (9) by again rotating the test element (1) and thus reach the membrane (12) via the channel (15). When the rotation is slowed down or stopped, the sample-reagent mixture is transported via the membrane (12) into the waste fleece (13).

The embodiments according to FIG. 2 and FIG. 4 differ in that a container for sample excess (7) is provided in FIG. 2 whereas the embodiment according to FIG. 4 does not provide such a function.

As in the embodiment according to FIG. 3, a metered application of the sample is expedient in this case.

FIG. 8 shows a variant of the embodiments according to FIGS. 2 and 4. In this case the sample is transferred by centrifugation into an erythrocyte separation structure (10, 11) directly after the sample application opening (4) after it has passed a first geometric valve (19). The area denoted (10) serves in this case as a serum/plasma collection zone (10) from which serum or plasma freed of cells after the centrifugation is transferred via a capillary channel (21). The chamber (20) serves as a collection reservoir for excess serum or plasma which may under certain circumstances continue to flow from the serum/plasma collection zone (10) after the sample metering section (5) has been completely filled. All other functions and structures are similar to FIGS. 1 to 7.

The hydrophilic or hydrophobic properties of the surfaces of the test element (1) can be selectively designed such that the sample liquid and/or washing liquid are moved either only with the aid of rotation and the resulting centrifugal forces or by a combination of centrifugal forces and capillary forces. The latter requires at least partially hydrophilized surfaces in the fluidic structures of the test element (1).

As already described further above in connection with FIG. 1, the test element according to the invention according to FIGS. 1, 2, 6, 7, 8 and 9 have an automatic functionality which allows a relatively accurate measurement of a sample aliquot from a sample that is applied to the test element in excess (so-called metering system). This metering system is a further subject matter of the present invention. It essentially comprises the elements 4, 5, 6 and 7 of the test elements (1) that are shown. Sample liquid and in particular whole blood is fed to the test element (1) via the sample application opening (4). The sample liquid fills the sample metering zone (5) driven by capillary forces and/or centrifugal forces. The sample metering zone (5) can in this connection also contain the dried reagents. It is delimited by the capillary stops (6 and 8) which can for example be in the form of hydrophobic barriers or geometric/non-closing valves. The delimitation of the sample metering zone (5) by the capillary stops (6, 8) ensures a defined sample volume is taken up and is passed into the fluidic zones that are located downstream of the sample metering zone (5). When the test element (1) is rotated, any sample excess is transferred from the sample application opening (4) and the sample metering zone (5) into the container for sample excess (7) whereas the metered amount of sample is transferred from the sample metering zone (5) into the channel (9). Alternatively it is also possible to use other forces for this purpose instead of the force generated by rotation which moves the sample e.g., by applying an overpressure on the sample input side or a negative pressure on the sample output side. The metering system shown is hence not imperatively tied to rotatable test elements but can also be used in other test elements.

Similar metering systems are known for example from U.S. Pat. No. 5,061,381. Also in this document a system is described in which sample liquid is applied in excess to a test element. In this case the metering of a relatively accurate sample aliquot which is subsequently processed further in the test element is also achieved by the interplay of a metering zone (metering chamber) and a zone for sample excess (overflow chamber) where, in contrast to the present invention, these two zones are in contact via a very narrow channel which always enables an exchange of liquid at least during filling. In this case sample liquid is immediately separated during the filling of the test element into a portion which is passed through a broad channel into the metering chamber, and a portion which flows through a narrow channel into the overflow chamber. After the metering chamber has been completely filled, the test element is rotated and any sample excess is diverted into the overflow chamber so that only the desired metered sample volume remains in the metering chamber which is subsequently processed further.

A disadvantage of the design of the metering system according to U.S. Pat. No. 5,061,381 is that in the case of sample volumes that are applied to the test element and correspond exactly to the minimum volume or are only slightly larger than the minimum volume, there is a risk that the metering zone will be underdosed because from the start a proportion of the sample always flows unhindered into the overflow chamber.

This problem is solved by the present proposed design of the metering system in that a capillary stop (hydrophobic barrier or a geometric or non-closing valve) is arranged between the metering zone and the zone for sample excess. Hence, when the test element is filled with sample, the sample is firstly practically exclusively passed into the metering zone. In this process the capillary stop prevents sample from flowing into the zone for sample excess before the sample metering zone is completely filled. Also in the case of sample volumes which are applied to the test element and exactly correspond to the minimum volume or are only slightly larger than the minimum volume, this ensures that the sample metering zone is completely filled.

In order that the invention may be more readily understood, reference is made to the following examples, which are intended to illustrate the invention, but not limit the scope thereof.

EXAMPLE 1

Preparation of a Test Element According to FIG. 6

1.1 Preparation of the Substrate (2)

A substrate (2) according to FIG. 6 (dimensions about 60×80 $mm^2$) is manufactured by means of injection molding from polycarbonate (PC) (alternatively polystyrene (PS), ABS plastic or poylmethylmethacrylate (PMMA) can also be used as the material). The individual channels and zones (fluidic structures) have the following dimensions (depth of the structures (d) and optionally their volumes (V); the numerals refer to FIG. 6 and the structures shown therein):

capillary between 4 and 5: d=500 μm
No. 7: d=700 μm
No. 5: d=150 μm; V=26.5 $mm^3$
No. 8: d=500 μm
No. 9: d=110 μm
No. 10: d=550 μm
No. 11: d=130 μm; V=15 $mm^3$
No. 15: d=150 μm; V=11.4 $mm^3$ A transition from less deep to deeper structures is usually only possible for liquids in the fluidic structures when force (e.g., centrifugal force) acts from outside. Such transitions act as geometric (non-closing) valves.

In addition to the fluidic structures (see above), the substrate (2) also has the sample and buffer addition openings (4, 16), vent openings (17) and the central opening (3).

The surface of the substrate (2) which has the fluidic structures can subsequently be cleaned by means of plasma treatment and hydrophilized.

1.2 Introducing the Reagents

Some of the reagents required for the analyte detection (e.g., biotinylated anti-analyte antibody and anti-analyte antibody labelled with a fluorescent label) are introduced alternately as a solution as point-shaped reagent spots in the sample metering section (5) by means of piezo metering and subsequently dried so that virtually the entire inner surface is occupied with reagents.

The composition of the reagent solutions is as follows:

| | |
|---|---|
| biotinylated antibody: | 50 mM Mes pH 5.6; 100 μg biotinylated monoclonal anti-troponin T antibody |
| labelled antibody: | 50 mM Hepes pH 7.4, containing a squaric acid derivative, fluorescent dye JG9 (embedded in polystyrene latex particles), fluorescent-labelled monoclonal anti-troponin T antibody (0.35% solution) |

1.3 Inserting the Membrane (12)

The porous matrix (12) (nitrocellulose membrane on a plastic carrier foil; 21×5 $mm^2$; cellulose nitrate membrane (type CN 140 from Sartorius, Germany) reinforced with 100 μm PE foil) into which an analyte detection line (polystreptavidin) and a control line (polyhapten) were introduced by means of line impregnation (see below) is inserted into a corresponding recess in the substrate (2) and optionally attached by means of double-sided adhesive tape.

An aqueous streptavidin solution (4.75 mg/ml) is applied to the cellulose nitrate membrane described above by line metering. For this purpose the dosage is selected (metered amount 0.12 ml/min, track speed 3 m/min) such that a line with a width of about 0.4 mm is formed. This line is used to detect the analyte to be determined and contains about 0.95 μg streptavidin per membrane.

An aqueous troponin T-polyhapten solution containing 0.3 mg/ml is applied at a distance of about 4 mm downstream of the streptavidin line under identical metering conditions. This line serves as a function control for the test element and contains about 0.06 μm polyhapten per test.

1.4 Applying the Cover

Subsequently the cover (foil or injection-molded part without fluidic structures which can optionally be hydrophilized) is applied and optionally permanently joined to the substrate (2) and typically glued, welded or clipped.

1.5 Inserting the Waste Fleece (13)

Finally the substrate is turned over and the waste fleece (13) (13×7×1.5 $mm^3$ fleece consisting of 100 parts glass fiber (diameter 0.49 to 0.58 μm, length 1000 μm) and 5 parts polyvinyl alcohol fibers (Kuralon VPB 105-2 from Kuraray) having a weight per unit area of about 180 $g/m^2$) is inserted into the corresponding recess and is then attached in the substrate (2) by means of an adhesive tape.

The quasi self-metering sample uptake unit (comprising the sample application opening (4), the sample metering section (5) and the adjoining structures (capillary stop (8) and container for sample excess (7)) ensures that irrespective of the amount of sample applied to the test element (1) (provided it exceeds a minimum volume (in this example 27 μl)) reproducibly identical sample amounts are used when using different test elements.

A homogeneous dissolution of the reagents in the entire sample volume is achieved by the distribution of the reagents in the entire sample metering section (5) typically in the form of alternating reagent spots (i.e., small, almost point-shaped reagent zones) in combination with a rapid filling of the sample metering section (5) with sample, especially if filling occurs considerably more rapidly than the dissolving. Moreover, there is a virtually complete dissolving of the reagents so that here again an increased reproducibility is observed in comparison to conventional test elements based on absorbent materials (test strips, bio-disks with reagent pads, etc.).

EXAMPLE 2

Detection of Troponin T with the Aid of the Test Element from Example 1

27 μl whole blood to which different amounts of recombinant troponin T were admixed were applied to the test element according to example 1. The test element is subsequently treated further according to the process stated in table 1 and finally the fluorescence signals for different concentrations are measured.

TABLE 1

| Measuring process | | | |
|---|---|---|---|
| Time (min:sec) | Duration (min:sec) | Rotation at revolutions per minute | Action |
| 00:00 | 01:00 | 0 | apply 27 μl sample; dissolve the reagents |
| 01:00 | 02:00 | 5000 | erythrocyte separation and incubation |
| 03:00 | 01:00 | 800 | chromatography (signal generation) |
| 04:00 | 00:10 | 0 | apply 12 μl washing buffer[1)] |
| 04:10 | 02:00 | 800 | washing buffer transport and chromatography |
| 06:10 | 00:10 | 0 | apply 12 μl washing buffer[1)] |
| 06:20 | 02:00 | 800 | washing buffer transport and chromatography |
| 08:20 | 00:10 | 0 | apply 12 μl washing buffer[1)] |
| 08:30 | 02:00 | 800 | washing buffer transport and chromatography |
| 10:30 | | 0 | Measure |

[1)]100 mM Hepes, pH 8.0; 150 mM NaCl; 0.095% sodium azide.

The measured data are shown in FIG. 10. The respective measured signals (in counts) are plotted against the concentration of recombinant troponin T (c(TnT)) in [ng/ml]). The actual troponin T concentration in the whole blood samples was determined with the reference method "Roche Diagnostics Elecsys Troponin T Test".

In comparison to conventional immunochromatographic troponin T test strips such as, e.g., Cardiac Troponin T from Roche Diagnostics, the detection limit for the measuring range that can be quantitatively evaluated is shifted downwards with the test element according to the invention (Cardiac Troponin T: 0.1 ng/ml; invention: 0.02 ng/ml) and the dynamic measuring range is extended upwards (Cardiac Troponin T: 2.0 ng/ml; invention: 20 ng/ml). The test elements according to the invention also show an improved precision.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A test element which is essentially disk-shaped, comprising:

an axis within the test element which is perpendicular to the plane of the test element and about which the test element is rotated;

a sample application opening for applying a liquid sample;

a capillary-active zone having a first end that is remote from the axis and a second end that is near to the axis, wherein the capillary-active zone is a porous, absorbent matrix and comprises one or more zones containing one or more immobilized reagents which specifically capture an analyte or species derived from or related to the analyte from the liquid sample flowing through the capillary-active zone and also immobilize the analyte or the species in the capillary-active zone; and a sample channel which extends from the sample application opening over an area near to the axis to the first end of the capillary-active zone that is remote from the axis, and wherein the sample channel contains an erythrocyte collecting zone for the separation of cellular blood components and a serum or plasma collection zone.

2. The test element according to claim 1, wherein the sample application opening is near to the axis and the sample channel extends from the sample application opening near to the axis to the first end of the capillary-active zone that is remote from the axis.

3. The test element according to claim 1, wherein the sample application opening is remote from the axis and is connected to an area near to the axis by a capillary channel.

4. The test element according to claim 1, wherein the porous, absorbent matrix is a paper, a membrane, or a fleece.

5. The test element according to claim 1, wherein the second end of the capillary-active zone is in contact with a further absorbent material or an absorbent structure which can receive the liquid from the capillary-active zone.

6. The test element according to claim 1, wherein the sample channel contains zones of different dimensions and/or for different functions.

7. The test element according to claim 1, wherein the sample channel contains a zone containing soluble reagents.

8. The test element according to claim 1, wherein the sample channel contains geometric valves or hydrophobic barriers.

9. The test element according to claim 1, wherein the sample channel contains a sample metering zone.

10. The test element according to claim 1, wherein the sample channel has an inlet for further liquids except for the sample liquid.

11. The test element according to claim 1, wherein the sample application opening is in contact with a sample metering zone and a zone for sample excess, and a capillary stop is present between the sample metering zone and the zone for sample excess.

12. A method for detecting an analyte in a liquid sample, comprising:

providing a test element which is essentially disk-shaped and comprises an axis within the test element which is perpendicular to the plane of the test element and about which the test element is rotated, a sample application opening for applying a liquid sample, a capillary-active zone having a first end that is remote from the axis and a second end that is near to the axis, wherein the capillary-active zone is a porous, absorbent matrix and comprises one or more zones containing one or more immobilized reagents which specifically capture an analyte or species derived from or related to the analyte from the liquid sample flowing through the capillary-active zone and also immobilize the analyte or the species in the capillary-active zone, and a sample channel which extends from the sample application opening over an area near to the axis to the first end of the capillary-active zone that is remote from the axis;

applying the sample to the sample application opening of the test element;

rotating the test element about the axis such that the sample is transported to the end of the capillary-active zone that is remote from the axis;

stopping or slowing the rotation of the test element to such an extent that the sample or a material obtained from the sample when it flows through the test element is sucked from the end remote from the axis to the end near to the axis of the capillary-active zone; and detecting the analyte visually or optically in the capillary-active zone or in a zone downstream thereof.

13. The method according to claim 12, wherein after the rotation of the test element, said method comprises applying a further liquid to the test element such that the further liquid is sucked after the sample from the first end to the second end of the capillary-active zone.

14. The method according to claim 13, further comprises selectively slowing down or stopping migration of at least one of the liquid sample and the further liquid through the capillary-active zone by the rotation of the test element.

15. The method according to claim 14, further comprises reversing the migration of at least one of the liquid sample and the further liquid through the capillary-active zone from the first end to the second end by the rotation of the test element.

16. A system for determining an analyte in a liquid sample comprising a test element according to claim 1 and a measuring device, wherein the measuring device has at least one drive for rotating the test element and an evaluation optics for evaluating the visual or optical signal of the test element.

17. The test element according to claim 1, wherein the second end is both nearer to the axis than the first end and located along a line extending from the axis to the first end such that migration of the liquid sample through the capillary-active zone from the first end to the second end is reversible by rotation of the test element about the axis.

18. The test element according to claim 1, wherein the axis is located at the center of the disc-shape of the test element.

* * * * *

UNITED STATES PATENT AND TRADEMARK OFFICE

CERTIFICATE OF CORRECTION

PATENT NO. : 8,470,588 B2
APPLICATION NO. : 12/407419
DATED : June 25, 2013
INVENTOR(S) : Christoph Boehm et al.

It is certified that error appears in the above-identified patent and that said Letters Patent is hereby corrected as shown below:

On the Title Page

Item (75) Christoph Boehm, “Viemheim (DE)” should read --Viernheim (DE)--; and

In the Claims

Col. 20, Claim 18, Line 21, “disc-shape” should read --disk-shape--.

Signed and Sealed this
Thirty-first Day of December, 2013

Margaret A. Focarino
*Commissioner for Patents of the United States Patent and Trademark Office*